United States Patent
Mimura et al.

(10) Patent No.: US 7,424,372 B2
(45) Date of Patent: Sep. 9, 2008

(54) METHOD AND APPARATUS FOR MEASURING PHYSICAL OR CHEMICAL PHENOMENA

(75) Inventors: Susumu Mimura, Kyoto (JP); Manabu Shibata, Kyoto (JP)

(73) Assignee: Horiba, Ltd., Kyoto (JP)

(*) Notice: Subject to any disclaimer, the term of this patent is extended or adjusted under 35 U.S.C. 154(b) by 122 days.

(21) Appl. No.: 11/289,819

(22) Filed: Nov. 29, 2005

(65) Prior Publication Data

US 2006/0129332 A1 Jun. 15, 2006

(30) Foreign Application Priority Data

Dec. 10, 2004 (JP) ............................. 2004-358803
Aug. 3, 2005 (JP) ............................. 2005-225505

(51) Int. Cl.
*G06F 19/00* (2006.01)
*H01L 29/78* (2006.01)

(52) U.S. Cl. ..................... 702/22; 257/253; 422/82.01

(58) Field of Classification Search .............. 702/22, 702/30, 57, 64, 65; 377/55–63; 341/150, 341/172; 257/253; 422/82.01
See application file for complete search history.

(56) References Cited

U.S. PATENT DOCUMENTS

| | | | |
|---|---|---|---|
| 5,852,347 A | | 12/1998 | Marcotte |
| 5,998,935 A | | 12/1999 | Marcotte |
| 6,255,678 B1 | * | 7/2001 | Sawada et al. ............... 257/253 |
| 6,294,133 B1 | * | 9/2001 | Sawada et al. ............ 422/82.01 |
| 6,342,874 B1 | | 1/2002 | Tokunaga et al. |

FOREIGN PATENT DOCUMENTS

| | | |
|---|---|---|
| DE | 198 57 851 | 7/1999 |
| EP | 0 881 486 | 12/1998 |
| EP | 1 130 389 | 9/2001 |
| EP | 1 278 060 | 1/2003 |
| JP | 07-296719 | 11/1995 |
| JP | 10-283934 | 10/1998 |
| JP | 10332423 | 12/1998 |
| WO | WO 03/043683 | 5/2003 |

OTHER PUBLICATIONS

Sawada, K. et al., "Highly sensitive ion using charge transfer technique", Sensors and Actuators B, Elsevier Sequoia, SA, Lausanne, CH, vol. 98, No. 1, Mar. 1, 2004, pp. 69-72.

* cited by examiner

*Primary Examiner*—John H Le (57) ABSTRACT

The present invention relates to a method of measuring a physical or chemical phenomenon by feeding electric charge from an charge feeding portion to a sensing portion having potential changed depending on the magnitude of physical or chemical amount, removing the fed electric charge via a floating diffusion from the sensing portion, and detecting the amount of the fed electric charge thereby measuring the physical or chemical phenomenon, which comprises allowing the electric charge from the sensing portion to be accumulated in a stage before the floating diffusion, to release a part thereof, and simultaneously transmitting, to the floating diffusion, the amount of electric charge containing the electric charge corresponding to the potential corresponding to the magnitude of physical or chemical amount, wherein the release amount of electric charge is changeable.

16 Claims, 8 Drawing Sheets

METHOD AND APPARATUS FOR MEASURING PHYSICAL OR CHEMICAL PHENOMENA

BACKGROUND OF THE INVENTION

1. Field of the Invention

The present invention relates to a measurement method and apparatus for quantifying physical or chemical phenomena and, for example, to a measurement method and apparatus for quantifying various physical or chemical phenomena such as the two-dimensional distribution of solution pH, pressure, magnetic field, or temperature.

2. Description of the Related Art

Physical or chemical phenomena include various phenomena such as concentration, temperature, magnetism, pressure, acceleration, speed, sound wave, supersonic wave, oxidation-reduction potential, and reaction rate, and these phenomena can be converted into various electric signals (electric current, voltage, resistance, electric charge capacity, and potential).

There is a method of measuring physical or chemical phenomena by converting them into electric charge information, such as a method of measuring the amount of light by converting the amount of light into the amount of electric charge and evaluating the amount of electric charge, by using a device such as a photodiode which upon irradiation with light forms a pair of electron holes corresponding to the amount of the light.

For measurement of physical and chemical phenomena other than light, however, the phenomena are converted in almost all cases not into the amount of electric charge but into electric signals such as voltage value, electric current value or resistance value, and these values are read, so accumulation and transmission, that is, processing methods unique to electric charge, is infeasible, and high-speed processing by simultaneous incorporation of information in a plurality of points, or conversion of measurement results into an image, is very difficult.

In various fields including environmental or medical fields, demand for such high-speed processing or conversion of physical or chemical phenomena into an image is increasing in recent years, and for example, there is proposed a method and apparatus for converting various physical or chemical phenomena easily into images, wherein a potential well constituted so as to have depth changed depending on the magnitude of physical or chemical amount is supplied with electric charge, and the physical or chemical amount is converted into electric charge depending on the magnitude of the potential well, whereby information in a plurality of points is simultaneously incorporated, followed by accumulation, transmission etc. (see, for example, JP-A 10-332423).

In measurement of physical or chemical phenomena at present, however, there is need for higher measurement accuracy and rapider response than before, and there is increasing demand for improvements in accuracy and response in the method and apparatus described above.

That is, when physical or chemical phenomena are converted into electric charge information, it is an urgent task to decide which constitution and structure are preferable for accuracy or response as the means of transferring electric charges in order to transfer electric charges efficiently and rapidly.

In measurement of physical or chemical phenomena, there are the case where a large amount of electric charges are transferred by a large change in phenomena and the case where a very small amount of electric charges are transferred due to a very small change in physical or chemical phenomena. In both the cases in actual measurement, a predetermined measurement accuracy corresponding to the change in phenomena is required, but under the transfer conditions of electric charges in both the cases, the same accuracy is hardly secured with detectors having the same constitution. That is, it is an urgent task for the detector to secure linearity in a broad range.

SUMMARY OF THE INVENTION

Under these circumstances, an object of the present invention is to provide a measurement method or a measurement apparatus having high measurement accuracy, excellent responsibility and excellent linearity by quantification of physical or chemical phenomena by conversion into electric charge information. Another object of the present invention is to provide a measurement method and a measurement apparatus which can easily convert various physical or chemical phenomena into images easily by simultaneously incorporating electric charge information in a plurality of points.

The present inventors made extensive study for solving the problem described above, and as a result they found that the object can be achieved by the following measurement method and measurement apparatus, and the present invention was thereby arrived at.

The present invention relates to a method of measuring a physical or chemical phenomenon by feeding electric charge from an charge feeding portion to a sensing portion having potential changed depending on the magnitude of physical or chemical amount, removing the fed electric charge via a floating diffusion from the sensing portion, and detecting the amount of the fed electric charge thereby measuring the physical or chemical phenomenon, which comprises allowing the electric charge from the sensing portion to be accumulated in a stage before the floating diffusion, to release a part thereof, and simultaneously transmitting, to the floating diffusion, the amount of electric charge containing the electric charge corresponding to the potential corresponding to the magnitude of physical or chemical amount, wherein the release amount of electric charge is changeable.

Further, the present invention relates to a method of measuring a physical or chemical phenomenon by feeding electric charge from an charge feeding portion to a sensing portion that is having potential changed depending on the magnitude of physical or chemical amount and is working as a threshold, removing the fed electric charge via a floating diffusion from the sensing portion, and detecting the amount of the fed electric charge thereby measuring the physical or chemical phenomenon, which comprises allowing the electric charge from the sensing portion to be accumulated in a stage before the floating diffusion, to release a part thereof, and simultaneously transmitting, to the floating diffusion, the amount of electric charge containing the electric charge corresponding to the potential corresponding to the magnitude of physical or chemical amount, wherein the release amount of electric charge is changeable.

Further, the present invention relates to an apparatus for measuring a physical or chemical phenomenon, which has an charge feeding portion for feeding electric charge to a sensing portion, a sensing portion having potential changed depending on the magnitude of physical or chemical amount, and a detection portion consisting of a floating diffusion for removing electric charge fed to the sensing portion, and which comprises, between the sensing portion and the floating diffusion, a sensing charge accumulation portion for accumulating electric charge transmitted from the sensing portion, a reset gate for releasing a part of the electric charge accumulated in the sensing charge accumulation portion, and a threshold portion for transmitting the remaining electric charge to the floating diffusion.

Further, the present invention relates to a measurement apparatus, which has a charge feeding portion for feeding electric charge to a sensing portion, a sensing portion having potential changed depending on the magnitude of physical or chemical amount and working as a threshold, and a detection portion consisting of a floating diffusion for removing electric charge fed to the sensing portion, and which comprises, between the sensing portion and the floating diffusion, a sensing charge accumulation portion for accumulating electric charge transmitted from the sensing portion, a reset gate for releasing a part of the electric charge accumulated in the sensing charge accumulation portion, and a threshold portion for transmitting the remaining electric charge to the floating diffusion.

The method of measuring a physical or chemical phenomenon by detecting the amount of electric charge with the sensing portion having potential (referred to hereinafter as "detection potential") changed depending on the magnitude of physical or chemical amount can convert the phenomenon into electric charge signals thereby enabling accumulation with easy addition and subtraction, and thus noises by averaging signals can be reduced. Further, the method is excellent in that the frequency of accumulation can be increased to enable detection of minute signals and to improve detection accuracy. Only the amount of electric charge (referred to hereinafter as "amount of measurement electric charge") corresponding to a change in physical or chemical amount is preferably detected.

In actuality, however, an electric charge (offset charge) not related to the measurement, or an electric charge (external disturbance) generated by influence from the vicinity of the detection system or from the electric charge processing system, for example an electric charge generated by the influence of temperature or a magnetic field or an electric field, is also detected. Particularly, there is a limitation in the capacity of the floating diffusion to which an electric charge from the sensing portion or an electric charge from the sensing portion working as a threshold is transmitted, so there is also a limitation in the frequency of accumulation for increasing detection sensitivity.

Accordingly, the present inventors examined the elimination of electric charges other than the amount of measurement electric charge, and as a result, they found that the external disturbing influence can be reduced and the S/N ratio can be improved effectively by accumulating an electric charge transmitted from the sensing portion or an electric charge transmitted from the sensing portion working as a threshold, then releasing a part of the electric charge and transmitting the remaining electric charge to the floating diffusion. That is, components other than the amount of measurement electric charge are reduced from the electric charge transmitted to the floating diffusion, whereby higher accumulation of measurement electric charge than before is made possible, noises are reduced, and the S/N ratio can be improved. Accordingly, linearity as detection property can be improved together with measurement accuracy.

An amount of the electric charge released from the electric charge accumulated in the stage before the floating diffusion can be usually determined from previously confirmed characteristics and set by the reset gate, and as described later, it is useful to regulate the amount of electric charge by the reset gate or the threshold portion.

Accordingly, there can be provided a measurement method or a measurement apparatus having high measurement accuracy, excellent responsibility and excellent linearity by quantification of physical or chemical phenomena by conversion into electric charge information.

The present invention relates to a method of measuring a physical or chemical phenomenon by a pair of detection systems consisting of a detection system A having a sensing portion having potential changed depending on the magnitude of physical or chemical amount and having the above function, and a detection system B having a sensing portion not responding with a change in physical or chemical amount and having the same function as that of the detection system A except for the sensing portion, wherein the amount of electric charge released in the detection system A is changed by synchronizing with the amount of the electric charge accumulated in the stage before the floating diffusion in the detection system B.

The present invention also relates to a measurement apparatus which comprises at least a pair of detection systems having a charge feeding portion, a sensing charge accumulation portion, and reset gates of the same structure as above, and which comprises:

a detection system A having a sensing portion having potential changed depending on the magnitude of physical or chemical amount, wherein a part of the electric charge fed to the sensing portion is transmitted via the sensing charge accumulation portion and a barrier portion to the floating diffusion, a detection system B having a sensing portion not responding to a change in physical or chemical amount and having the same function as in the detection system A except for the sensing portion, wherein the amount of electric charge transmitted from the barrier portion in the detection system A is changed by synchronizing with the amount of electric charge accumulated in the sensing charge accumulation portion in the detection system B.

When the physical or chemical phenomenon is converted into electric charge information, measurement accuracy and linearity as detection property are improved effectively by reducing components other than the amount of measurement electric charge and preferably by simultaneously carrying out compensation by synchronizing with the change in the components. In the present invention, a dual detection system is used, and potential not related to the measurement is detected in one detection system B, and the difference of this potential from the detection potential in the other detection system A is obtained, whereby the potential which should be truly detected can be detected. That is, the detection system has differential functions in it thereby enabling prevention of the influence of further external disturbance during compensation.

Specifically, the potential of the threshold portion in the detection system A is changed by synchronizing with the amount of electric charge (that is, offset charge and external disturbing components) accumulated in the sensing charge accumulation portion in the detection system B, and the amount of electric charge transmitted to the floating diffusion (that is, the amount of electric charge released from the reset gate) is changed, whereby the influence of components other than the amount of measurement electric charge can be effectively eliminated. Accordingly, a measurement method or a measurement apparatus having high measurement accuracy, excellent responsibility and excellent S/N ratio can be provided.

The present invention relates to an apparatus for measurement of a physical or chemical phenomenon, which is provided with a charge transmission means between the sensing charge accumulation portion and the floating diffusion, wherein the charge transmission means is a charge coupled device, and the electric charge in a plurality of sensing charge accumulation portions is transmitted to one floating diffusion.

With respect to a semiconductor device for detecting physical or chemical phenomena, the potential of the floating diffusion can be increased as "electric charge capacity of the sensing portion"/"electric charge capacity of the floating diffusion" is increased. Accordingly, the degree of amplification can be increased, and accurate and highly sensitive measurement is feasible. On the other hand, there is a limit because of the structural limitation. In the present invention, a charge transmission portion is arranged therebetween, whereby the sensing portion and the floating diffusion can be constituted in an arbitrary shape or arrangement, and detection sensitivity and response rate can be easily improved.

Generally, there are various methods as the means of transmitting electric charges in the semiconductor device, and a charge coupled device (CCD) has excellent properties in respect of high S/N ratio, rate of transmission, efficiency of transmission, and operativeness. Accordingly, the apparatus of the present invention has a CCD function of transferring electric charges one after another from a plurality of sensing portions (more specifically, sensing charge accumulation portions) via the charge transmission portion to one floating diffusion, whereby one- or two-dimensional distribution of physical or chemical phenomena can be easily converted into an image.

The present invention relates to an apparatus for measurement of a physical or chemical phenomenon, comprising the detection portion having n-diffusion layer formed, or, when the semiconductor portion is p-type substrate, having an electrode constituted on the upper site of the p-type substrate to form a sensing charge accumulation portion.

Generally, on a semiconductor device for an apparatus for measurement of a charge, a surface-type or bulk-type channel of is formed. In the former a large amount of electric charges can be processed, but the transmission loss may be generated. On the other hand, in the latter the transmission loss is not generated above described because of transmitting between channels via the inner of the bulk (n-type diffusion layer) of the substrate.

This invention can rapidly transfer the electric charges by forming n-type diffusion layer for decreasing the transmission loss to provide a measurement apparatus having high measurement accuracy and excellent responsibility. And the detection portion can be made having the same functional ability as n-type diffusion layer formed, by having an electrode constituted on the upper site of the p-type substrate to form a sensing charge accumulation portion without forming n-type diffusion layer on the semiconductor substrate.

According to the method or apparatus for measurement of physical or chemical phenomena according to the present invention as described above, electric charges accompanying physical or chemical phenomena as the subject, or output generated thereby, can be amplified, while information in a plurality of points can be simultaneously incorporated to effect accumulation, transmission etc., whereby detection accuracy can be improved, response speed can be increased, and various physical or chemical phenomena can be easily converted into an image.

Particularly, the amount of electric charge transmitted to the floating diffusion is converted into electric charge information corresponding truly to physical or chemical phenomena, whereby further high accuracy and higher speed can be achieved. The two-dimensional distribution of physical or chemical phenomena can be easily converted into an image by using CCD etc. Particularly, a faint signal can be amplified, and thus a faint change in physical or chemical phenomena from information in a plurality of points can also be easily grasped.

DETAILED DESCRIPTION OF THE INVENTION

Embodiments of the invention will be described with reference to the drawings.

<Fundamental constitution of the apparatus for measurement of physical or chemical phenomena>

Figure 1:
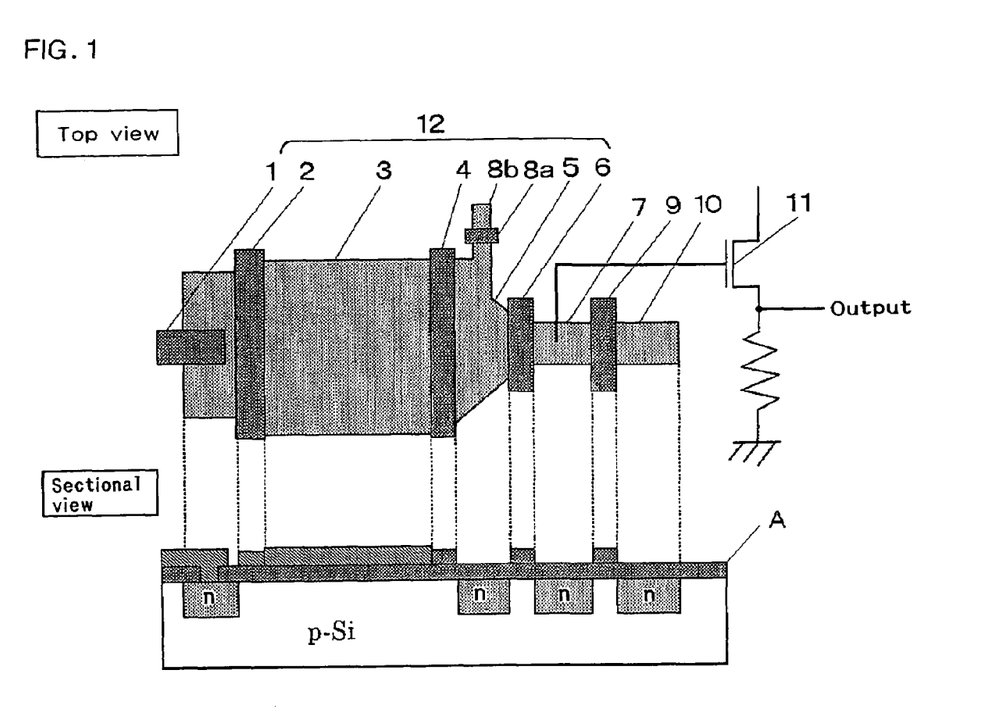
FIG. 1 is a diagram showing a fundamental structure (first constitutional example) of a detecting portion of the measurement apparatus according to the present invention.
Figure 2:
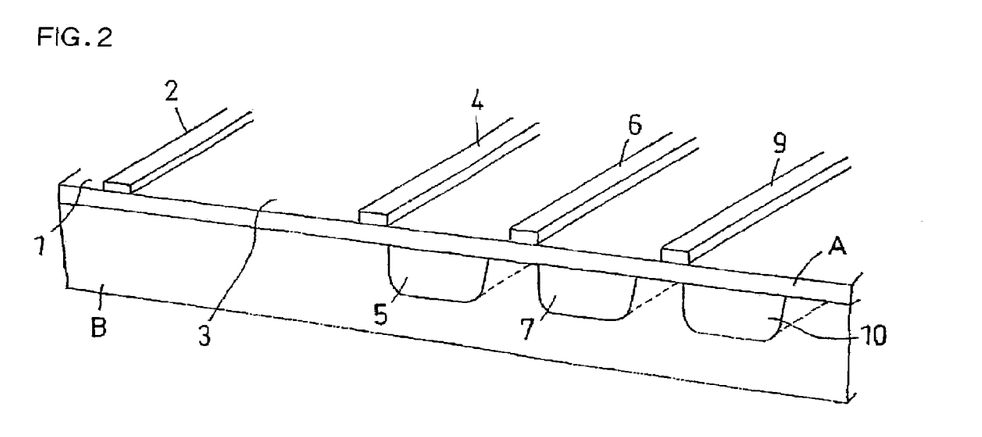
FIG. 2 is a diagram schematically showing an essential portion of a detection portion of the measurement apparatus according to the present invention.

FIG. 1 illustrates a fundamental constitution of the apparatus for measurement of physical or chemical phenomena according to the present invention, and FIG. 2 is a perspective view thereof (first constitutional example).

In FIG. 1 or 2, B is for example a semiconductor substrate made of p-type Si (silicon) having a thickness of about 500 mm. The semiconductor substrate B has, for example, an insulating film A consisting of a silicon oxide film on which a charge feeding portion 1, a charge feeding regulation portion 2, a sensing portion 3, a barrier portion 4, a sensing charge accumulation portion 5, a threshold portion 6, a floating diffusion 7, reset gates 8a and 9, reset drains 8b and 10, and an output transistor 11 are formed. A sensor portion 12 is formed by each member of the charge feeding portion 1, charge feeding regulation portion 2, sensing portion 3, barrier portion 4, reset gate 8a, reset drain 8b, sensing charge accumulation portion 5, and threshold portion 6, and a detection portion is formed by the sensor portion 12, floating diffusion 7, reset gate 9, and reset drain 10. The semiconductor substrate B is endowed with resistance to a solution sample etc. by providing it with a resin mold.

In measurement, pulse voltage is applied to the charge feeding portion 1, barrier portion 4, threshold portion 6, and reset gates 8a and 9, while direct-current voltage is applied to the other sites, and positive voltage is applied to an MOS structure using a p-type semiconductor, whereby a potential state can be formed in the vicinity of the semiconductor/insulating film interface.

The sensor portion 12 is formed for example in the following manner.

(1) A p-type Si substrate B is thermally oxidized to form an oxide film (SiO2).
(2) A part thereof is etched and then selectively oxidized. Thereafter, SiO2 in the selectively oxidized part is etched and further thermally oxidized thereby forming a gate oxide film A. The thickness of the gate oxide film is about 500 Å.
(3) Low-density polysilicon doped with phosphorus is deposited on the portions corresponding to the charge feeding regulation portion 2, barrier portion 4 or threshold portion 6 respectively, to form an electrode. The thickness of this electrode is about 3000 Å, and after deposition, the electrode is thermally oxidized to a thickness of about 1000 Å.
(4) Thereafter, low-density polysilicon doped with phosphorus is deposited again to form an electrode on the upper surface of the sensing charge accumulation portion 5. This electrode is deposited to have similar thickness to that described above, and then thermally oxidized to a thickness of about 1000 Å. By oxidation in this manner, the insulation between the electrodes can be maintained. This electrode is substitutable to be made by Al, W, Ti. However, this electrode is not needed in the case of n-diffusion layer formed as shown in FIG. 1; when the semiconductor portion is p-type substrate, a sensing charge accumulation portion 5 needs the electrode.
(5) Thereafter, about 700 Å Si3N4 (otherwise Ta2O3 or Al2O3) is deposited thereon to form a sensing portion 3.

The sensing portion 3 is a measurement site having potential changed depending on the magnitude of physical or chemical amount, and in the case of pH measurement, for example, an electrode portion provided with a cell into which an aqueous solution or a measurement object is introduced is formed to generate potential corresponding to the pH of the sample. The potential, or a change in the potential, is converted into electric charge, and the change in electric charge in the detection portion is outputted and converted by the output transistor 11 of MOS structure.

The number of the charge feeding portion 1 per one sensing portion 3 is not limited to 1, and a plurality of charge feeding portions 1 may be arranged. As described above, the number, shape or arrangement relationship of sensing portions 3 may be unconditionally determined depending on a measurement object or applications, and when the feed of electric charge to the whole of the sensing portion 3 should be rapidly carried out, loading of electric charge into the sensing portion 3 is preferably dispersed into a plurality of charge feeding portions 1.

The sensing charge accumulation portion 5 is established depending on the shape of the sensing portion 3 or the charge capacity ratio of the sensing portion 3 to the sensing charge accumulation portion 5, and in FIG. 1, a trapezoid shape is formed so that the contact area with the sensing portion is increased, while the area of the sensing charge accumulation portion 5 is decreased. The sensing charge accumulation portion 5 may be formed by n-diffusion layer or p-type substrate as it is.

The floating diffusion 7 can be made significantly smaller than before because its size is determined on the basis of the portion contacting with the sensing charge accumulation portion 5, and electric charge excluding the electric charge released in the sensing charge accumulation portion 5 is transmitted. In FIG. 1, the floating diffusion 7 is square, but if the shape of the sensing charge accumulation portion 5 is square, the floating diffusion 7 can be formed in a trapezoid shape so that the contacting portion with the sensing charge accumulation portion 5 is increased, while the area of the floating diffusion 7 is decreased.

The measurement method in the measurement apparatus described above is explained by reference to a potential diagram shown in FIG. 3(A).

(1) Initial Potential State

Initially, the potential of the charge feeding portion 1 is set high (namely, arrow direction is high potential), and no electric charge is fed to the sensing portion 3.

(2) Feed of Electric Charge

By decreasing the potential of the charge feeding portion 1, electric charge is fed to the sensing portion 3.

(3) Accumulation of Electric Charge

By increasing the potential of the charge feeding portion 1, a part of the fed electric charge overflows so that the amount of electric charge limited by the charge feeding regulation portion 2 is accumulated in the sensing portion 3. The amount of electric charge thus accumulated in the sensing portion 3 contains offset charge y and external disturbing component z in addition to the amount x of measurement electric charge, as shown in FIG. 3(B).

(4) Electric Charge Transmission 1

By increasing the potential of the barrier portion 4, the electric charge accumulated in the sensing portion 3 is transmitted to the sensing charge accumulation portion 5.

(5) Electric Charge Transmission 2

By decreasing the potential of the barrier portion 4 and increasing the potential of the threshold portion 6, a part of the electric charge accumulated in the sensing charge accumulation portion 5 is transmitted to floating diffusion 7. The amount of electric charge thus transmitted is mainly the amount x of measurement electric charge, but further contains offset charge y or external disturbing component z.

(6) Electric Charge Release

By increasing the potential of a reset gate 8a, the electric charge accumulated in the sensing charge accumulation portion 5 is released via a reset drain 8b to the outside.

(7) Accumulation Cycle

The above-mentioned (2) to (6) are carried out repeatedly until a predetermined amount of electric charge is accumulated in the floating diffusion 7. By this repetition, noises such as external disturbance can be averaged, and the so-called random noise can be substantially reduced. The frequency of this repetition is the substantial degree of amplification in this detection system. An accurate description of the degree of amplification will be described later. The threshold portion 6 can be in the same state while electric charge is repeatedly accumulated. Given less change in the offset charge, external disturbing noises can be averaged and compensation for offset charge is feasible.

(8) Measurement of Electric Charge

When a predetermined amount of electric charge is accumulated in the floating diffusion 7 or when the number of times the accumulation cycle (7) was repeated reaches a predetermined number, the potential of the threshold portion 6 is lowered and closed to terminate the inflow of electric charge. In this stage, the potential of the floating diffusion 7 is determined by the amount of electric charge transmitted, so this potential is input into the gate portion in the output transistor 11 of MOS structure, and the drain electric current in this output transistor 11 is measured.

(9) Reset

After the voltage of the floating diffusion 7 is read, the reset gate 9 is turned ON, thus supplying electric charge from the reset drain 10 and resetting the potential of the floating diffusion 7 to the potential of the reset drain 10.

(10) Detection Cycle

By the reset mentioned above, the apparatus is returned to the same state again as in (1). That is, the detection cycle involves repeating the operations in (1) to (9) thereby enabling sequent output of the amount of electric charge corresponding to the state of the potential in the sensing portion 3.

As described above, this measurement apparatus makes use of a charge conversion mechanism in which the sensing portion 3 constituted so as to have charge changed depending on the magnitude of physical or chemical amount is formed on the semiconductor substrate B, and electric charge is fed to the sensing portion 3, and the physical or chemical amount is converted into electric charge corresponding to the size of the sensing portion 3. By the reset gate 8a arranged on the sensing charge accumulation portion 5, the offset potential or external disturbing component can be released so that the amount of measurement charge can be detected under conditions where factors as noises in detection of the amount of measurement charge are reduced to the lowest degree.

Figure 3:
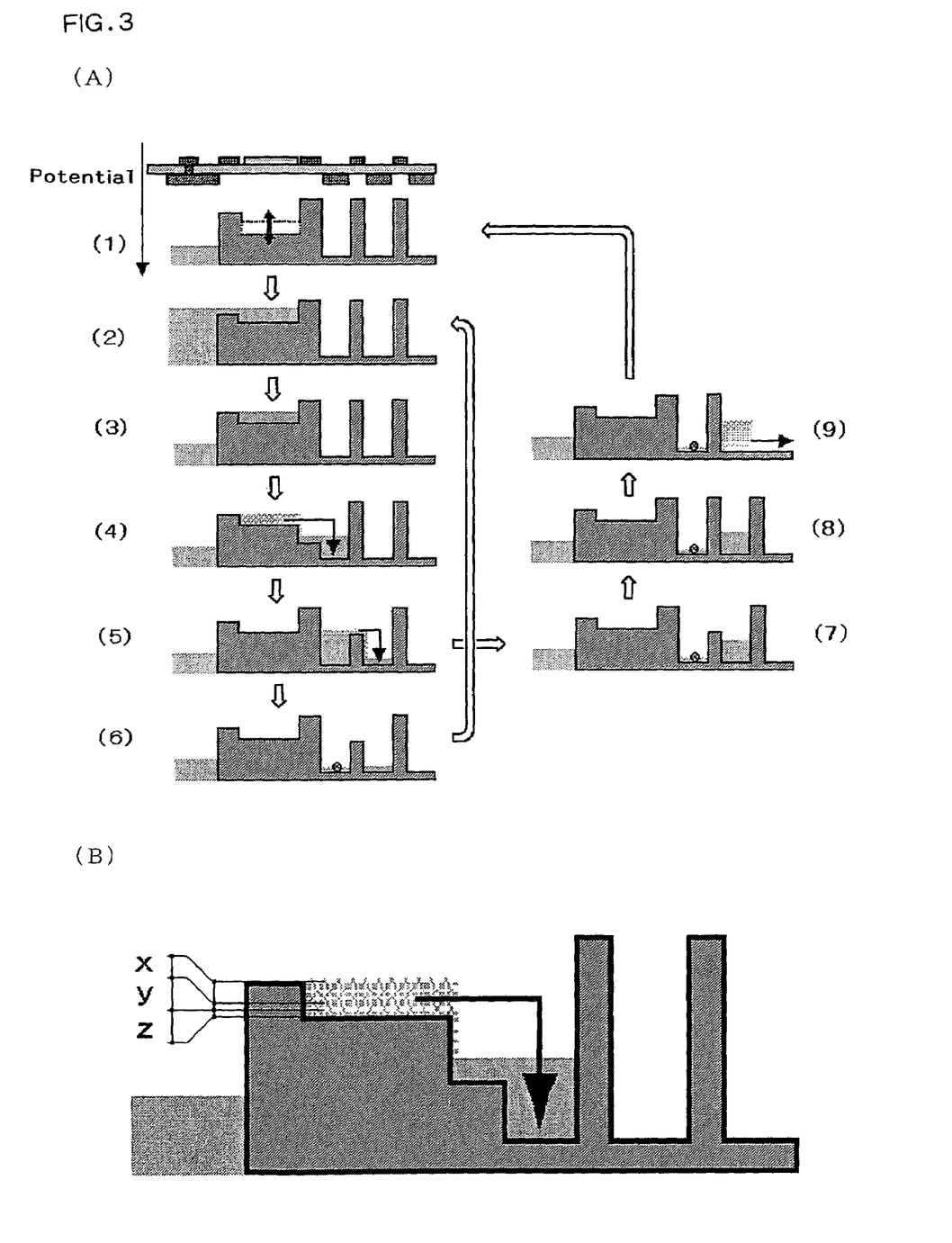
FIG. 3 is a diagram illustrating one potential change according to the measurement method of the present invention.
Figure 4:
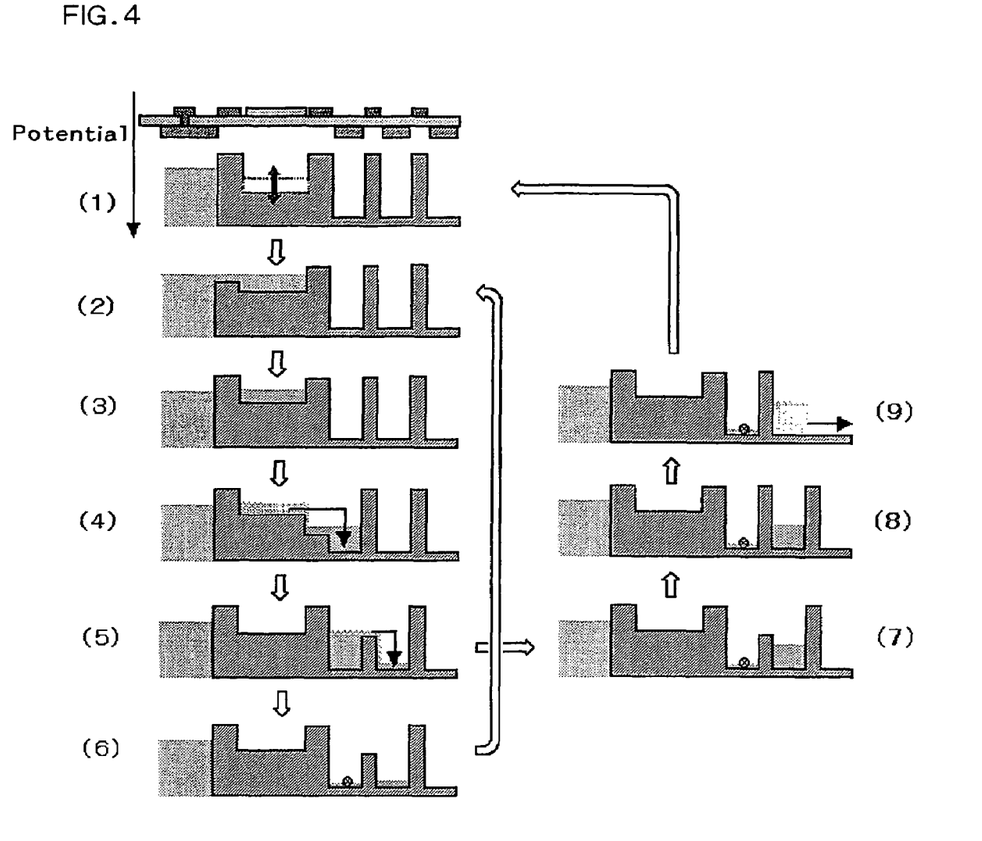
FIG. 4 is a diagram illustrating another potential change according to the measurement method of the present invention.

The amplification degree A in the measurement can be accurately expressed by the following formula 1:

$$A = \frac{\sum_{i=1}^{n} Q_i / C_{FD}}{\Delta V_S}$$ [Formula 1]

wherein:

Q [C]: the amount of electric charge transmitted once to the floating diffusion n [times]: the frequency of accumulation CFD [F]: the electric charge capacity of the floating diffusion DVS: change in the potential of the sensing portion In FIG. 3(A), the electric charge accumulated in the sensing portion 3 is cut by increasing and decreasing the potential of the charge feeding portion 1, but alternatively electric charge may be accumulated in the sensing portion 3 by increasing and decreasing the height of the charge feeding regulation portion 2 while the potential of the charge feeding portion 1 is kept constant, as shown in FIG. 4. That is, the physical or chemical amount can be stably converted into electric charge corresponding to the size of the sensing portion 3 by the following operation.

(1) Initial Potential State

Initially, the potential of the charge feeding portion 1 is set lower than that of the sensing portion 3, and the potential of the charge feeding regulation portion 2 is set further lower, and the sensing portion 3 is not supplied with electric charge.

(2) Feed of Electric Charge

The potential of the charge feeding regulation portion 2 is increased so as to be higher than the potential of the charge feeding portion 1 thereby feeding electric charge to the sensing portion 3.

(3) Accumulation of Electric Charge

The potential of the charge feeding regulation portion 2 is reduced to the state in (1), whereby the fed electric charge is accumulated in the sensing portion 3.

(4) Electric Charge Transmission 1

By increasing the potential of the barrier portion 4, the electric charge accumulated in the sensing portion 3 is transmitted to the sensing charge accumulation portion 5.

(5) Electric Charge Transmission 2

By increasing the potential of the threshold portion 6, a part of the electric charge accumulated in the sensing charge accumulation portion 5 is transmitted to the floating diffusion 7. The amount of electric charge thus transmitted is mainly the amount of measurement electric charge, but futher contains some amount of the offset charge or external disturbing component.

(6) Electric Charge Release

By increasing the potential of the reset gate 9, the electric charge accumulated in the sensing charge accumulation portion 5 is released to the outside.

(7) Accumulation Cycle

The above-mentioned (2) to (6) are carried out repeatedly until a predetermined amount of electric charge is accumulated in the floating diffusion 7. By this repetition, noises such as external disturbance can be averaged, and the so-called random noise can be substantially reduced. The frequency of this repetition is the substantial degree of amplification in this detection system. The threshold portion 6 can be in the same state while electric charge is repeatedly accumulated. Given less change in the offset charge, external disturbing noises can be averaged and compensation for offset charge is feasible.

(8) Measurement of Electric Charge

When a predetermined amount of electric charge is accumulated in the floating diffusion 7 or when the number of times the accumulation cycle (7) was repeated reaches a predetermined number, the potential of the threshold portion 6 is lowered and closed to terminate the inflow of electric charge. In this stage, the potential of the floating diffusion 7 is determined by the amount of electric charge transmitted, so this potential is input into the gate portion in the output transistor 11 of MOS structure, and the drain electric current in this output transistor 11 is measured.

(9) Reset

After the potential of the floating diffusion 7 is read, the reset gate 9 is turned ON, thus supplying electric charge from the reset drain 10 and resetting the potential of the floating diffusion 7 to the potential of the reset drain 10.

(10) Detection Cycle

By the reset mentioned above, the apparatus is returned to the same state again as in (1). That is, the detection cycle involves repeating the operations in (1) to (9) thereby enabling sequent output of the amount of electric charge corresponding to the state of the potential in the sensing portion 3. Together with the advantage of the method in FIG. 3(A), further improvement in stability can be achieved by retaining a predetermined potential by using the potential of the charge feeding portion 1 as standard. Like FIG. 3(A), electric charge near to the amount of electric charge corresponding substantially to the chemical or physical phenomenon only is transmitted from the electric charge accumulated in the sensing portion 3 to the floating diffusion 7, and can thus processed as an electric charge signal with less noise component.

In the present invention, the electric charge capacity of the sensing portion 3 preferably has a size exceeding the electric charge capacity of the floating diffusion 7. For example, the detection cycle mentioned above is carried out repeatedly until a certain amount of electric charge is accumulated in the floating diffusion 7, and then the electric charge is measured, whereby detection sensitivity can be increased, but the response time is delayed by the accumulation time. By increasing the electric charge capacity of the sensing portion 3 to increase the amount of electric charge to be accumulated, the rate of change in the potential in the floating diffusion 7 can be increased upon transmission to the floating diffusion 7 with small electric charge capacity, so accurate and highly sensitive measurement is feasible by detecting the rate of change. That is, the apparatus comes to have a function of substantially amplifying a change in the potential in the sensing portion 3 by providing it with a difference in electric charge capacity between the sensing portion 3 and the floating diffusion 7 as charge transmission means.

For increasing the electric charge capacity of the sensing portion 3, there are specific means wherein (1) the area on a plane is increased, (2) a plurality of sensing portions 3 are used, (3) potential is increased, and (4) charge density is increased, from which a suitable means can be selected depending on the state or concentration of a sample as a subject of physical or chemical phenomenon.

Figure 4A:
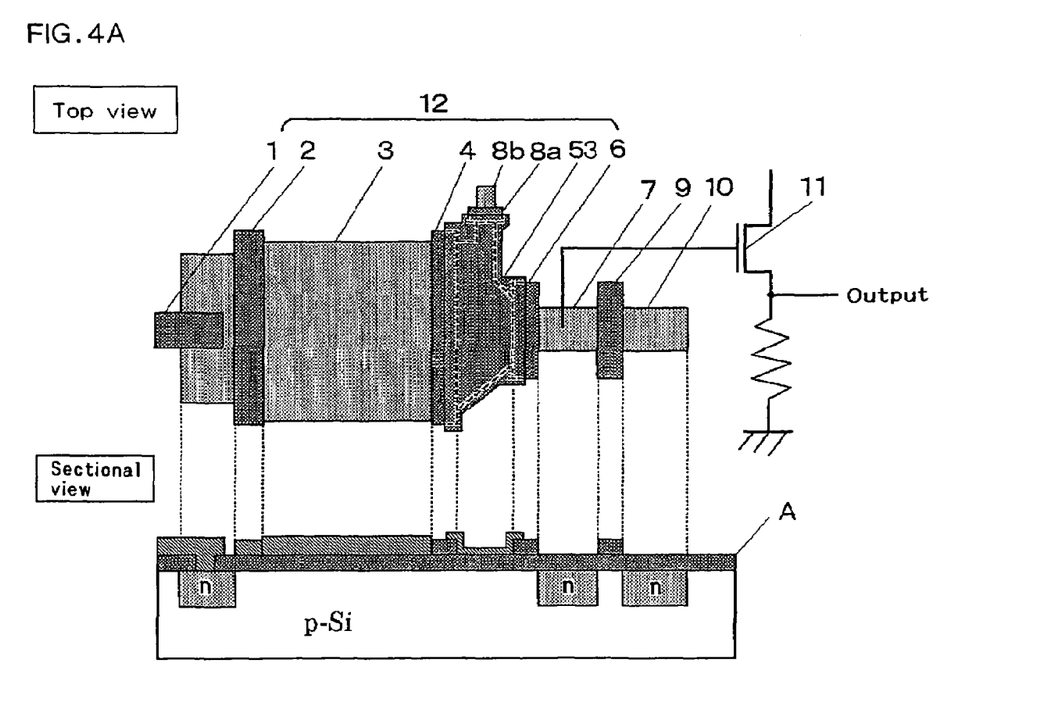
FIG. 4A is a diagram illustrating another embodiment of the sensing charge accumulation portion of the first constitutional example.

The constitutional example having the semiconductor portion formed the p-type substrate and having an electrode constituted on a sensing charge accumulation portion is illustrated in FIG. 4A. The first constitutional example having a sensing charge accumulation portion 5 formed n-type diffusion layer does not need the electrode, on the other side, the constitution illustrated in FIG. 4A have the same functional ability as above, by having an electrode constituted on the upper site of the p-type substrate to form a sensing charge accumulation portion 53 without forming n-type diffusion layer. Then the metal material constituted on this upper site can be used, for example metal such as Al, W, T or poly-Si. This measurement method is similar to that illustrated in FIG. 3(A), so the description about it is omitted.

Now, the second constitutional example in the present invention is described. When the potential of the sensing portion 3 is made considerably lower than a predetermined value (that is, negatively changed) in the first constitutional example, the amount of electric charge accumulated in the sensing charge accumulation portion 5 can be low, and the electric charge transmitted from the threshold portion 6 to the floating diffusion 7 can be lower than the amount x of measurement electric charge. In this case, the sensing portion 3 is worked as a threshold in place of the charge feeding regulation portion 2 in FIG. 1, thus making the amount of accumulated electric charge changeable so as to correspond to physical or chemical phenomena, in order that the electric charge corresponding to the potential of the sensing portion 3 is accumulated in the sensing charge accumulation portion 5.

Figure 5:
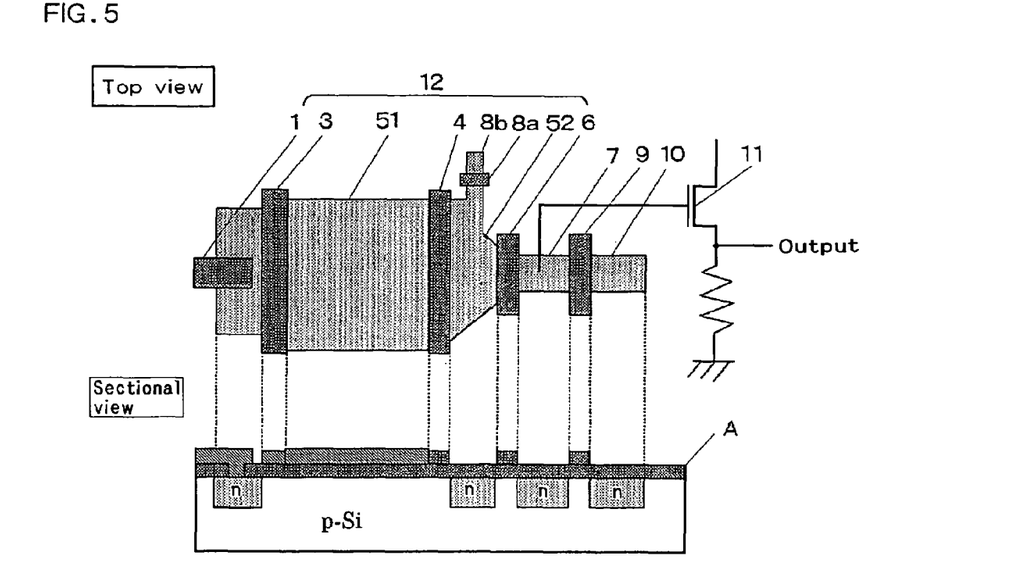
FIG. 5 is a diagram illustrating a second constitutional example according to the present invention.

Specifically, as shown in FIG. 5, the potential in the sensing portion 3 can be worked as a threshold so that even if the potential of the sensing portion 3 is negatively changed, a change in the amount of electric charge fed from the charge feeding portion 1 to the sensing charge accumulation portion 51 can be taken out according to the chemical or physical phenomenon generated in the sensing portion 3. The constitutions and functions of the barrier portion 4, the sensing charge accumulation portion 52 and the portions thereafter are the same as in the first constitutional example. When the potential of the sensing portion 3 is stably changed, electric charge can be accumulated directly in the sensing charge accumulation portion 52 by omitting the sensing charge accumulation portion 51 and the barrier portion 4.

Figure 6:
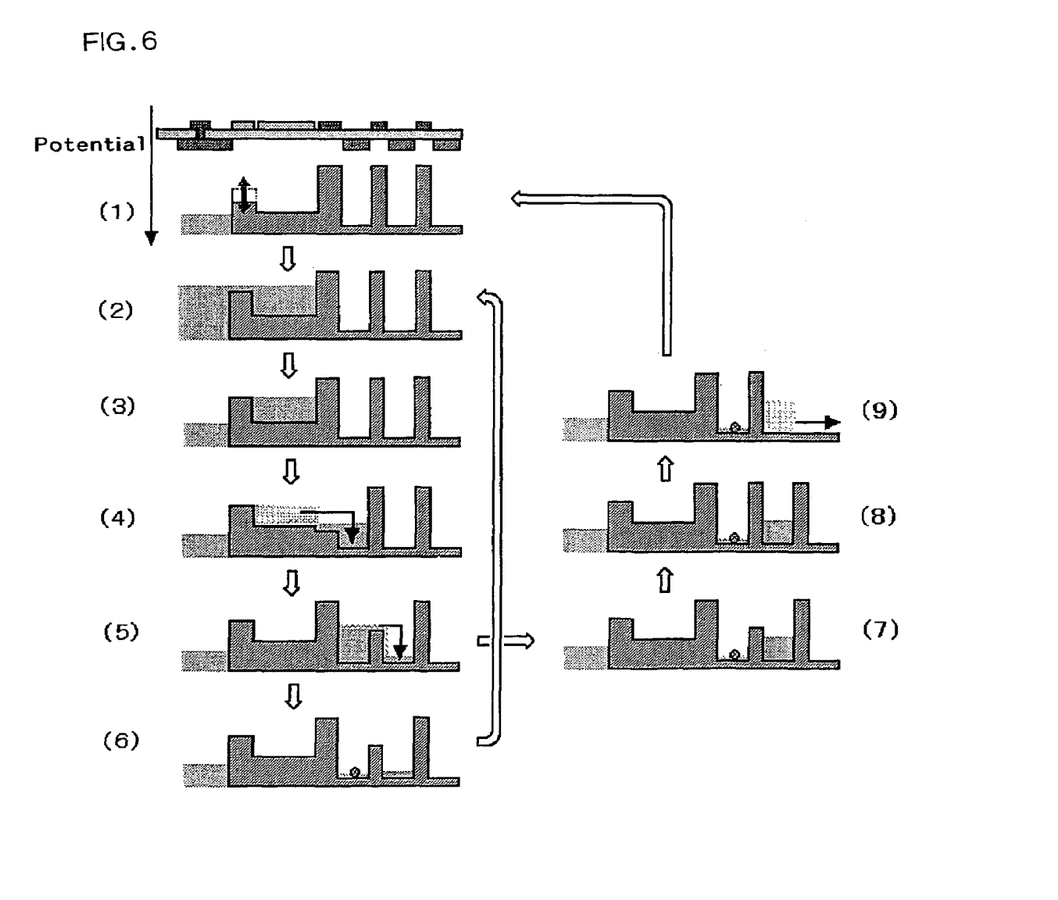
FIG. 6 is a diagram illustrating one potential change according to the measurement method in the second constitutional example.

The measurement method in the measurement apparatus described above is described by reference to a potential diagram shown in FIG. 6.

(1) Initial Potential State

Initially, the potential of the charge feeding portion 1 is set high (namely, arrow direction is high potential), and no electric charge is fed to the sensing charge accumulation portion 51.

(2) Feed of Electric Charge

By decreasing the potential of the charge feeding portion 1, electric charge is fed via the sensing portion 3 worked as a threshold to the sensing charge accumulation portion 51.

(3) Accumulation of Electric Charge

By increasing the potential of the charge feeding portion 1, a part of the fed electric charge overflows so that the amount of electric charge limited by the sensing portion 3 worked as a threshold is accumulated in the sensing charge accumulation portion 51. The amount of electric charge thus accumulated in the sensing charge accumulation portion 51 contains an offset charge y and an external disturbing component z in addition to the amount x of measurement electric charge.

(4) Electric Charge Transmission 1

By increasing the potential of the barrier portion 4, the electric charge accumulated in the sensing charge accumulation portion 51 is transmitted to the sensing charge accumulation portion 52.

(5) Electric Charge Transmission 2

By decreasing the potential of the barrier portion 4 and increasing the potential of the threshold portion 6, a part of the electric charge accumulated in the sensing charge accumulation portion 52 is transmitted to the floating diffusion 7. The amount of electric charge thus transmitted is mainly the amount x of measurement electric charge, but further contains the offset charge y or the external disturbing component z.

(6) Electric Charge Release

By increasing the potential of the reset gate 8a, the electric charge accumulated in the sensing charge accumulation portion 52 is released via the reset drain 8b to the outside.

(7) Accumulation Cycle

The above-mentioned (2) to (6) are carried out repeatedly until a predetermined amount of electric charge is accumulated in the floating diffusion 7. By this repetition, noises such as external disturbance can be averaged, and the so-called random noise can be substantially reduced. The frequency of this repetition is the substantial degree of amplification in this detection system.

(8) Measurement of Electric Charge

When a predetermined amount of electric charge is accumulated in the floating diffusion 7 or when the number of times the accumulation cycle (7) was repeated reaches a predetermined number, the potential of the threshold portion 6 is lowered and closed to terminate the inflow of electric charge. In this stage, the potential of the floating diffusion 7 is determined by the amount of electric charge transmitted, so this potential is input into the gate portion in the output transistor 11 of MOS structure, and the drain electric current in this output transistor 11 is measured.

(9) Reset

After the voltage of the floating diffusion 7 is read, the reset gate 9 is turned ON, thus supplying electric charge from the reset drain 10 and resetting the potential of the floating diffusion 7 to the potential of the reset drain 10.

(10) Detection Cycle

By the reset mentioned above, the apparatus is returned to the same state again as in (1). That is, the detection cycle involves repeating the operations in (1) to (9) thereby enabling sequent output of the amount of electric charge corresponding to the state of the potential in the sensing portion 3.

As described above, this measurement apparatus makes use of a charge conversion mechanism in which the sensing portion 3 constituted so as to have charge changed depending on the magnitude of physical or chemical amount is formed on the semiconductor substrate B, and electric charge is fed via the sensing portion 3 worked as a threshold, and the physical or chemical amount is converted into the amount of electric charge transferred. By the reset gate 8a arranged on the sensing charge accumulation portion 52, the offset potential or external disturbing component can be released so that the amount of measurement charge can be detected under conditions where factors as noises in detection of the amount of measurement charge are reduced to the lowest degree.

In FIG. 5, the electric charge accumulated in the sensing portion 3 is cut by increasing and decreasing the potential of the charge feeding portion 1, but alternatively the potential of the charge feeding portion 1 is kept constant, and electric charge may be accumulated in the sensing charge accumulation portion 51, so as to correspond to the potential of the sensing portion 3 (not shown in the figure).

Figure 7:
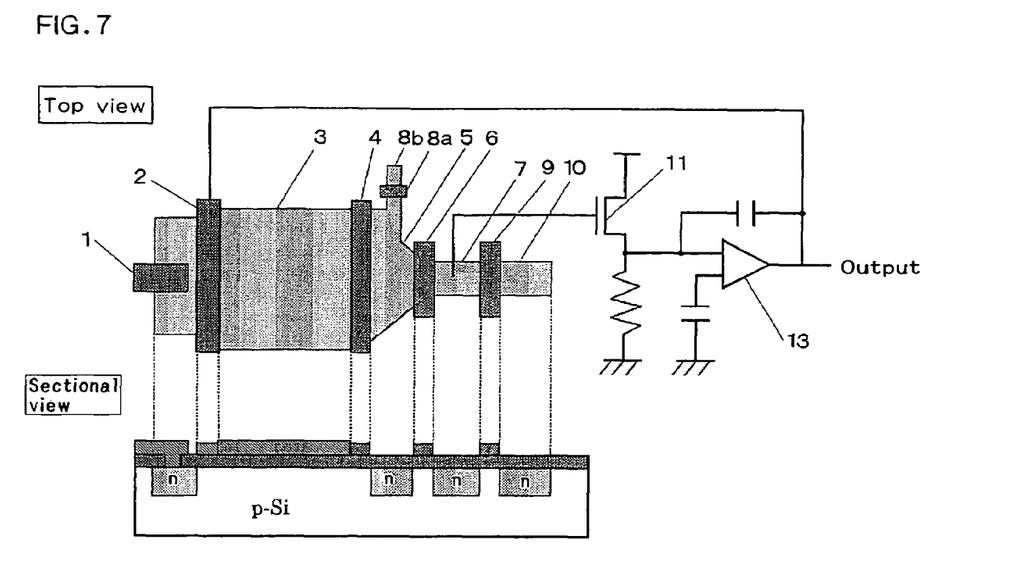
FIG. 7 is a diagram showing a third constitutional example according to the present invention.

The third constitutional example in the present invention is illustrated in FIG. 7. The output side of the output transistor 11 is provided with a feedback circuit 13 (regulation portion), and the potential of the charge feeding regulation portion 2 is regulated such that the output of the output transistor 11 becomes constant, and the regulation amount is converted into a measurement value.

That is, when quantification is performed by converting the physical or chemical phenomenon into electric charge information, the influence of electric charge remaining the sensing portion 3 or floating diffusion 7 may not be negligible. Specifically, when the distance of charge transfer from the sensing portion 3 to the floating diffusion 7 is long or when the time of detection cycle is short, charge transfer cannot be caught up, so a part of the electric charge may remain in the sensing portion 3. In highly sensitive measurement monitoring the transfer of minute electric charge, linearity, particularly linearity in the vicinity of zero, may be worsened. In the present invention, therefore, the potential of the charge feeding regulation portion 2 is regulated such that the amount of electric charge transferred is made constant by setting the amount of electric charge so as to prevent the electric charge from remaining in the sensing portion 3 or not to influence detection properties even if the electric charge remains.

That is, when the potential difference between the charge feeding regulation portion 2 and the sensing portion 3 is made constant, the amount of electric charge fed to the sensing portion 3 can be made constant, and the amount of electric charge transferred is made constant. When the amount of electric charge transferred is made higher than a predetermined value, the influence of the remaining electric charge can be negligible. That is, when the amount of electric charge transferred is higher than a predetermined amount, the transmission power drops with time, and thus the probability of remaining electric charge (the transmission loss) is increased. On the other hand, when a predetermined amount of transmission loss is generated during actual transmission and the amount of electric charge transferred is lower than a predetermined amount, its influence cannot be negligible.

The amount of electric charge transferred from the sensing portion 3 to the floating diffusion 7 becomes constant, and as a result, the potential of the floating diffusion 7 becomes constant. That is, when the potential of the charge feeding regulation portion 2 is regulated depending on the change in the potential of the sensing portion 3 accompanying the physical or chemical phenomenon such that the output of the output transistor 11 arranged in the floating diffusion 7 becomes constant, the amount of the regulated potential can become a measurement amount corresponding to the change in the physical or chemical phenomenon, and excellent detection properties having linearity can be obtained.

When the amount of electric charge transferred in the sensor portion 12 is made constant, the functions of the sensor portion 12 can be stabilized by reducing fluctuation factors. Even if the characteristics of the sensing portion 3 are varied, the above operation can be carried out on the basis of the potential of the charge feeding regulation portion 2 regulated such that the potential difference between the sensing portion 3 and the charge feeding regulation portion 2 is made constant for the same sample. Accordingly, the similar output characteristics can be obtained without strictly regulating the characteristics of the sensing portion 3.

<Fundamental constitution of a dual apparatus for measurement of physical or chemical phenomena>

Figure 8:
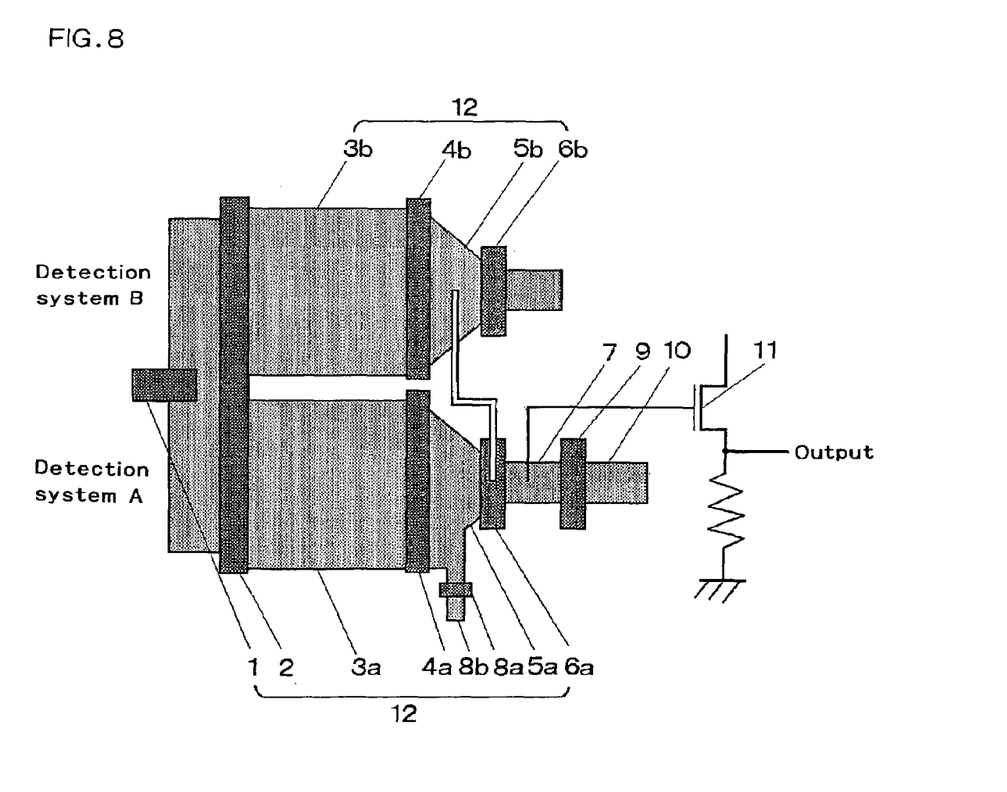
FIG. 8 is a diagram showing a fourth constitutional example according to the present invention.

Now, a dual measurement apparatus to which the above-described fundamental apparatus for measurement of physical or chemical phenomena is applied is described. The fundamental constitution of the dual apparatus for measurement of physical or chemical phenomena (fourth constitutional example) is illustrated in FIG. 8.

The apparatus is characterized basically in that two parallel detection systems having the detection portion in the constitutional example described above are constituted, and one threshold portion 6a is connected to the other sensing charge accumulation portion 5b to have the same potential as in. The apparatus comprises two detection systems using one charge feeding portion 1 and one charge feeding regulation portion 2 in common, and one detection system A is composed of a sensing portion 3a having potential changed depending on a physical or chemical phenomenon, a barrier portion 4a, a sensing charge accumulation portion 5a, a threshold 6a, a floating diffusion 7, reset gates 8a and 9, reset drains 8b and 10, and an output transistor 11. The other detection system B is composed of a sensing portion 3b not responding to a physical or chemical phenomenon, a barrier portion 4b, a sensing charge accumulation portion 5b, and a threshold portion 6b. The sensing portions 3a and 3b form basically the same structure, and are provided preferably with a film or site having a different responding property to a physical or chemical phenomenon. This is because the compensation function of the detection system B can be improved by generating the same change in offset charge and external disturbing component.

In measurement, the electric charge signal in the detection system A corresponds to "detection signal+offset signal+external disturbing signal", while the electric charge signal in the detection system B corresponds to "offset signal+external disturbing signal". Accordingly, the true "detection signal" can be obtained by determining the difference between the two. That is, in the present invention, the amount of electric charge to be accumulated in the sensing charge accumulation portion 5a in the detection system A corresponds to the electric charge signal in the detection system A described above, and the amount of electric charge accumulated in the sensing charge accumulation portion 5b in the detection system B corresponds to the electric charge signal in the detection system B described above. The threshold portion 6a in the detection system A and the sensing charge accumulation portion 5b in the detection system B are connected at the same potential, and thus the amount of electric charge to be accumulated in the sensing charge accumulation portion 5a in the detection system A minus the amount of electric charge accumulated in the sensing charge accumulation portion 5b in the detection system B, that is, the amount of electric charge corresponding to the detection signal only is transmitted via the threshold 6a in the detection system A to the floating diffusion 7. Accordingly, the truly required detection signal only can be taken out with high accuracy by effectively using the compensation function of the detection system B.

The measurement method in the fourth constitutional example is described by reference to a potential diagram shown in FIG. 9.

(1) Initial Potential State

Initially, the potential of the charge feeding portion 1 is set high (namely, arrow direction is high potential), and no electric charge is fed to the sensing portions 3a and 3b.

(2) Feed of Electric Charge

By decreasing the potential of the charge feeding portion 1, electric charge is fed to the sensing portions 3a and 3b.

(3) Accumulation of Electric Charge 1

By increasing the potential of the charge feeding portion 1, a part of the fed electric charge overflows so that the amount of electric charge limited by the charge feeding regulation portion 2 is accumulated in the sensing portions 3a and 3b. The amount of electric charge thus accumulated in the sensing portion 3a in the detection system A contains an offset charge y and an external disturbing component z in addition to the amount x of measurement electric charge as shown in FIG. 3(B), and the amount of electric charge corresponding to the offset charge y and the external disturbing component z is accumulated in the sensing portion 3b in the detection system.

(4) Electric Charge Transmission 1

By increasing the potential of the barrier portions 4a and 4b, the electric charge accumulated in the sensing portions 3a and 3b is transmitted to the sensing charge accumulation portions 5a and 5b. Preferably, the potential of the barrier 4a in the detection system A is increased with slight delay after the potential of the barrier portion 4b in the detection system B is increased. The potential of the threshold portion 6a becomes the same level as the potential of the sensing charge accumulation portion 5b, so the potential of the threshold portion 6a is gradually decreased in accordance with the increase in the amount of electric charge accumulated in the sensing charge accumulation portion 5b. By increasing the potential of the barrier portion 4a with slight delay after the potential of the barrier layer 4b is increased, the potential of the threshold portion 6b in the detection system A is increased thereby forming a space for accumulating the electric charge from the sensing portion 3a, thus preventing the electric charge from being transmitted by leakage into the floating diffusion 7. The delay time can be previously established by measuring or estimating the amount x of the measurement electric charge, the offset charge y and the external disturbing component z.

(5) Accumulation of Electric Charge 2

By decreasing the potential of the barrier portions 4a and 4b, a part of the electric charge accumulated is accumulated in the sensing charge accumulation portions 5a and 5b. The amount of electric charge in the sensing charge accumulation portion 5b in the detection system B contains the offset charge y or the external disturbing component z. On the other hand, the amount of electric charge accumulated in the sensing charge accumulation portion 5a in the detection system A contains the offset charge y or the external disturbing component y originally in addition to the amount x of the measurement electric charge.

(6) Electric Charge Transmission 2

However, since the potential of the threshold portion 6a is not made lower than the potential of the sensing charge accumulation portion 5b, the amount x of the measurement electric charge overflows from the threshold portion 6a and is transmitted to the floating diffusion 7.

(7) Electric Charge Release

By increasing the potential of the reset gate 8a, the electric charge accumulated in the sensing charge accumulation portion 5a in the detection system A is released to the outside. By increasing the potential of the threshold portion 6b, the electric charge accumulated in the sensing charge accumulation portion 5b in the detection system B is released to the outside.

(8) Accumulation Cycle

The above-mentioned (2) to (7) are carried out repeatedly until a predetermined amount of electric charge is accumulated in the floating diffusion 7. By this repetition, noises such as external disturbance can be averaged, and the so-called random noise can be substantially reduced. The frequency of this repetition is the substantially degree of amplification in this detection system. In the present invention, the amount of detected electric charge only can be extracted and accumulated, and thus the S/N ratio is significantly improved.

(9) Measurement of Electric Charge

When a predetermined amount of electric charge is accumulated in the floating diffusion 7 or when the number of times the accumulation cycle (8) was repeated reaches a predetermined number, the potential of the threshold portion 6a is lowered and closed to terminate the inflow of electric charge. In this stage, the potential of the floating diffusion 7 is determined by the amount of electric charge transmitted, so this potential is input into the gate portion in the output transistor 11 of MOS structure, and the drain electric current in this output transistor 11 is measured.

(10) Reset

After the voltage of the floating diffusion 7 is read, the reset gate 9 is turned ON, thus supplying electric charge from the reset drain 10 and resetting the potential of the floating diffusion 7 to the potential of the reset drain 10.

(11) Detection Cycle

By the reset mentioned above, the apparatus is returned to the same state again as in (1). That is, the detection cycle involves repeating the operations in (1) to (10) thereby enabling sequent output of the amount of electric charge corresponding to the state of the potential in the sensing portion 3a.

In this measurement apparatus described above, the amount of electric charge free from noise components, that is, the offset charge and external disturbing component, is taken out from the electric charge from the sensing portion 3a constituted to have potential changed depending on the magnitude of physical or chemical amount, whereby the amount of measurement charge can be detected under conditions where factors as noises in detection of the amount of the measurement charge are reduced to the lowest degree.

Figure 9:
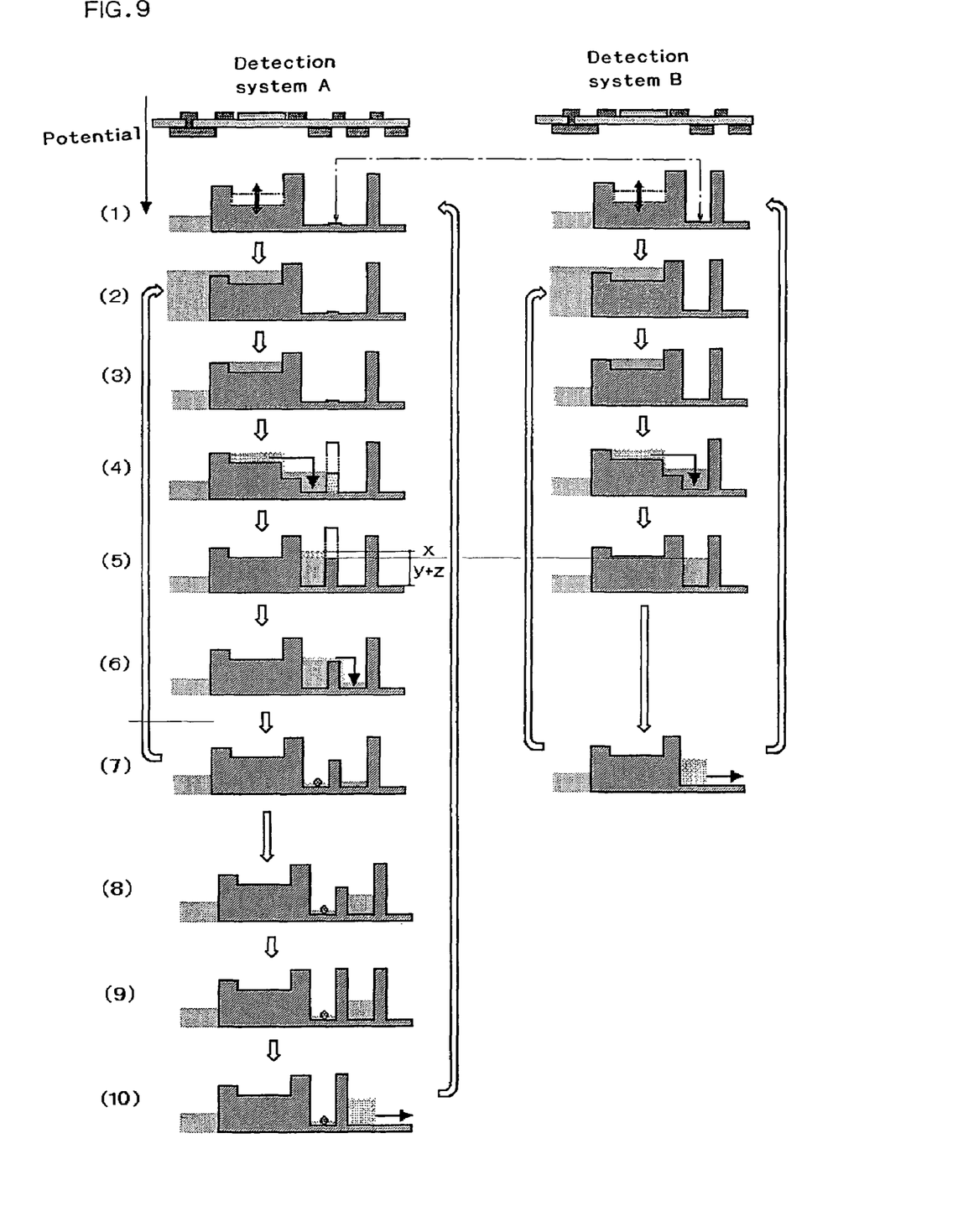
FIG. 9 is a diagram illustrating one potential change according to the measurement method in the fourth constitutional example.

In FIG. 9, the electric charge accumulated in the sensing portion 3 is cut by increasing and decreasing the potential of the charge feeding portion 1, but alternatively the potential of the charge feeding portion 1 is kept constant, and electric charge may be accumulated in the sensing portions 3a and 3b by increasing and decreasing the height of the charge feeding regulation portion 2 (not shown in the figure).

Figure 10:
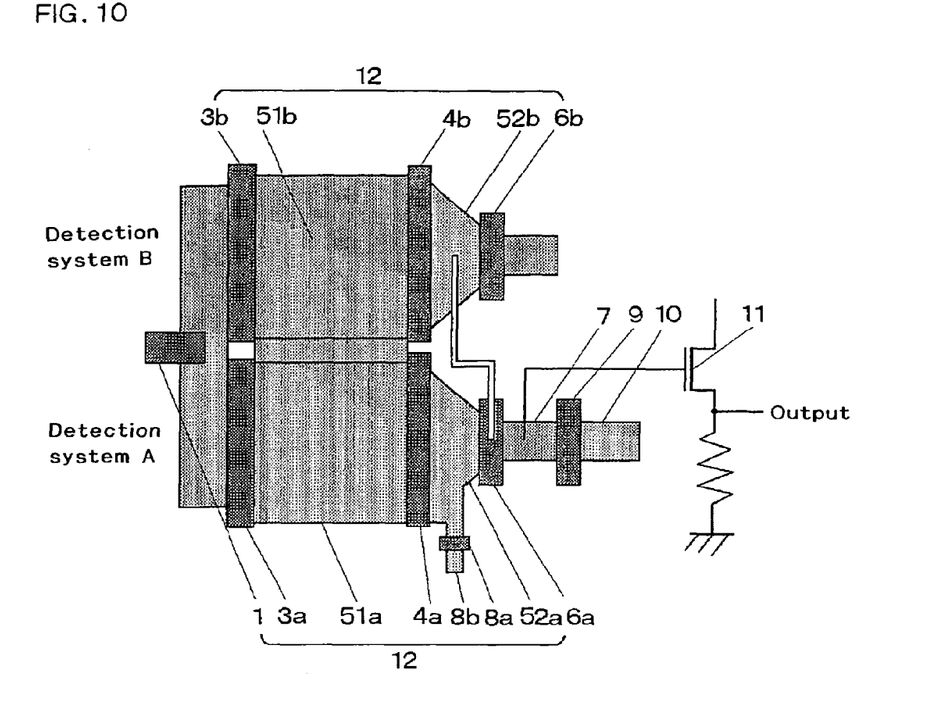
FIG. 10 is a diagram illustrating a fifth constitutional example according to the present invention.

The fifth constitutional example, wherein each detection system is based on the second constitutional example, is now described, while in the fourth constitutional example, each detection system is based on the constitution of the first constitutional example.

As illustrated in FIG. 10, the fifth constitutional example is the same as in the fourth constitutional example in respect of the fundamental constitution, but is different in that the amount of electric charge fed to the sensing charge accumulation portions 51a and 51b is determined with a pair of sensing portions 3a and 3b worked as thresholds in two detection systems A and B in place of the charge feeding regulation portion.

That is, even if the potential of the sensing portions 3a and 3b are negatively changed corresponding to a chemical or physical phenomenon or due to a change in offset and external disturbance, the change, corresponding to the chemical or physical phenomenon, of the amount of electric charge fed from the charge feeding portion 1 to the sensing charge accumulation portions 51a and 51b can be taken out in the detection system A with the sensing portion 3a worked as a threshold, while the change not corresponding to the chemical or physical phenomenon can be taken out in the detection system B with the sensing portion 3b worked as a threshold.

As shown in FIG. 10, the sensing charge accumulation portions 51a and 51b preferably have the same potential. This is because the offset charges y in the respective detection systems can be made equal such that the compensation function can be improved.

Specifically, the amount of electric charge fed to the sensing charge accumulation portion 51a in the detection system A is mainly the amount x of the measurement electric charge, but further contains the offset charge y or the external disturbing component z. On the other hand, the amount of electric charge fed to the sensing charge accumulation portion 51b in the detection system B contains the offset charge y or the external disturbing component z. Accordingly, with respect to the respective amounts of electric charge transmitted from the sensing charge accumulation portions 51a and 51b, the threshold portion 6a in the detection system A and the sensing charge accumulation portion 52b in the detection system B are connected at the same potential, and thus the amount of electric charge to be accumulated in the sensing charge accumulation portion 52a in the detection system A minus the amount of electric charge accumulated in the sensing charge accumulation portion 52b in the detection system B, that is, the amount x of the measurement electric charge only is transmitted via the threshold portion 6a in the detection system A to the floating diffusion 7. Accordingly, only the truly required amount x of the measurement electric value, that is, the detection signal only can be taken out with high accuracy by effectively using the compensation function of the detection system B.

Figure 11:
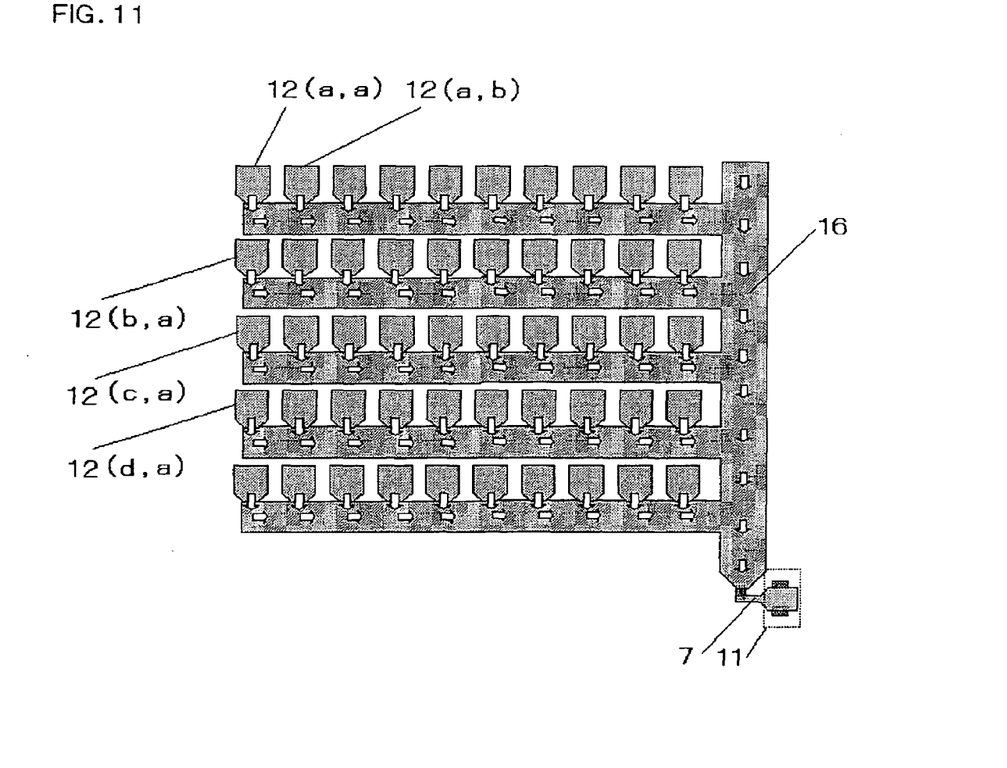
FIG. 11 is a diagram illustrating a sixth constitutional example according to the present invention.

The apparatus may have a CCD function of transferring electric charges one after another from a plurality of sensors via the charge transmission portion to one floating diffusion, whereby one- or two-dimensional distribution of physical or chemical phenomena can be converted easily into an image. Specifically, the sixth constitutional example as shown in FIG. 11 is feasible.

That is, the apparatus comprises a plurality of sensor portions 12(a, a), 12(a, b), . . . , a charge transmission portion 16 for transmitting, in the array direction, the electric charge converted in each sensor portion, one floating diffusion 7 for further transmitting the transmitted electric charge, and an output transistor 11 for converting the transmitted electric charge into an output signal.

By arranging an array of the sensor portions 12(a, a), 12(a, b), . . . one- or two-dimensionally, information in a plurality of points is simultaneously incorporated so that signals in a plurality of points can be processed orderly by the charge transmission portion 16 and the output transistor 11. The outputted signals are outputted into an image output unit (not shown in the figure) such as CRT to output an image, or the outputted signals are converted into AD and inputted into a computer.

That is, gates in connection portions between the sensor portions 12(a, a), 12(a, b), . . . and the charge transmission portion 16 are opened one after another to supply the accumulated electric charge which is then transmitted via the transmission path of the charge transmission portion 16 by turning the CCD driving potential ON-OFF in order. For driving CCD in the transmission portion 16, one-phase driving, two-phase driving or four-phase driving can be suitably selected depending on the amount of electric charge transmitted. The efficiency of transmission becomes problematic as the number of sensor portions 12 is increased, and in this case, a bulk channel having high efficiency of transmission is preferably used as the transmission path. The charge transmitted is transmitted to the floating diffusion 7, to change the potential of the floating diffusion 7. This change in the potential is inputted as detection output into the gate of the output transistor 11.

CCD has excellent properties in respect of high S/N ratio, rate of transfer, efficiency of transmission, and operativeness, and is very useful in actuating a plurality of electrodes. That is, the CCD is also superior in that a plurality of electrodes constituting the CCD can perform the functions of the sensing charge accumulation portion 5, the barrier portion 4 or the threshold portion 6, to achieve higher transmission. The CCD is also useful in that since there is no necessity for providing a difference among voltages applied to the respective electrodes, there is no necessity for limitation of the potential difference between the sensing portion 3 and the floating diffusion 7 or for limitation of the number of electrodes. In the CCD, the number of electrodes driven during transmission of electric charge can be changed depending on the amount of electric charge accumulated in the sensing portion 3 thereby transmitting electric charge under the optimum conditions. That is, when the amount of electric charge transmitted is too high, a plurality of electrodes are driven whereby electric charge not transmitted can be eliminated. When the amount of electric charge transmitted is low, one electrode can be driven whereby the remaining electric charge in the electrode portion can be eliminated, thus eliminating a cause for measurement errors.

In the foregoing description, the present invention has been described by reference to the constitutional examples wherein the functions formed by the invention according to each claim are partially combined, but as a matter of course, the present invention can be carried out in any other combinations or any arbitrary combinations with the features described in the present application.

As described above, the present invention can be applied preferably not only in two-dimensional distribution measurement of ion concentration in various samples such as solution, but also to the following fields:

(1) Application fields as a chemical microscope, chemical; ion concentration measurement, electrochemical field; two-dimensional dynamic observation and analysis of gas distribution measurement field and titration
(2) Environmental measurement, environment; application to bio-remediation
(3) Food examination, food, microorganism
(4) ME field, medicine, biological tissue; measurement of surface ion concentration in tissue cells, cell surface potential measurement, DNA measurement
(5) Biological field
(6) Animal and plant field, plant; measurement of surface potential distribution in callus, living creatures, front view animal
(7) Corrosion measurement field, metal; metallic corrosion and paint, coating
(8) Surface analysis of zeta potential etc., powder and ceramic zeta potential.

The measurement object (sample) may be a gas, liquid, solid and powder, and the present invention can be applied to chemical sensing reacting selectively by a specific responsive layer of the sensor portion, and any phenomena showing charge fluctuation in interfacial phenomena by physical contact, and for example, distribution of a transient phenomenon in liquid stream or in an instant chemical reaction can be obtained as a chemical image of high density and high qualities. Further, the present invention is useful not only in real-time imaging of titration phenomenon but also in another kind of analysis and display by imaging software, and also useful in pocket cameras.

What is claimed is:

1. A method of measuring a physical or chemical phenomenon comprising:
    feeding electric charge from a charge feeding portion to a sensing portion having potential changed depending on the magnitude of physical or chemical amount, removing the fed electric charge via a charge accumulation region and a floating diffusion region from the sensing portion, and detecting the amount of the fed electric charge by allowing the electric charge from the sensing portion to be accumulated in a charge accumulation portion before entering the floating diffusion region, to release a part of the electric charge that is corresponding to an offset potential or external disturbing component, and
    simultaneously transmitting, to the floating diffusion region, the amount of electric charge containing the electric charge corresponding to the potential corresponding to the magnitude of physical or chemical amount,
    measuring a physical or chemical phenomenon by a pair of detection systems consisting of a detection system A having a sensing portion having potential changed depending on the magnitude of physical or chemical amount, and a detection system B having a sensing portion not responding to a change in physical or chemical amount and having the same function as that of the detection system A except for the sensing portion,
    wherein the amount of electric charge released in the detection system A is changed by synchronizing with the amount of the electric charge accumulated in the stage before the floating diffusion region in the detection system B and wherein the release amount of electric charge is changeable.

2. A method of measuring a physical or chemical phenomenon comprising:
    feeding electric charge from a charge feeding portion to a floating diffusion region via a sensing portion that is having potential changed depending on the magnitude of physical or chemical amount and is working as a threshold, removing the fed electric charge via the floating diffusion region, and detecting the amount of the fed electric charge by allowing the electric charge, that is fed from the charge feeding portion and limited by a sensing portion threshold to accumulate in a stage before the floating diffusion region, to release a part of the electric charge that is corresponding to an offset potential or external disturbing component, and simultaneously transmitting, to the floating diffusion region, the amount of electric charge containing the electric charge corresponding to the potential corresponding to the magnitude of physical or chemical amount, wherein the release amount of electric charge is changeable,
    measuring a physical or chemical phenomenon by a pair of detection systems consisting of a detection system A having a sensing portion having potential changed depending on the magnitude of physical or chemical amount, and a detection system B having a sensing portion not responding to a change in physical or chemical amount and having the same function as that of the detection system A except for the sensing portion,
    wherein the amount of electric charge released in the detection system A is changed by synchronizing with the amount of the electric charge accumulated in the stage before the floating diffusion region in the detection system B.

3. An apparatus for measuring a physical or chemical phenomenon, comprising:
    a charge feeding portion for feeding electric charge to a sensing portion, the sensing portion having voltage changed depending on the magnitude of physical or chemical amount, and a detection portion having a floating diffusion region for removing electric charge fed to the sensing portion,
    a sensing charge accumulation portion interposed between the sensing portion and the floating diffusion region, the sensing portion accumulating electric charge transmitted from the sensing portion and having a reset gate for releasing a part of the electric charge that is corresponding to an offset potential or external disturbing component, and
    a threshold portion for transmitting the remaining electric charge to the floating diffusion region,
    a detection system A having a sensing portion having potential changed depending on the magnitude of physical or chemical amount, wherein a part of the electric charge fed to the sensing portion is transmitted via the sensing charge accumulation portion and a barrier portion to the floating diffusion region,
    a detection system B having a sensing portion not responding to a change in physical or chemical amount and having the same function as in the detection system A except for the sensing portion,
    wherein the amount of electric charge transmitted from the barrier portion in the detection system A is changed by synchronizing with the amount of electric charge accumulated in the sensing charge accumulation portion in the detection system B.

4. The apparatus for measurement of a physical or chemical phenomenon according to claim 3, further comprising a charge transmission means between the sensing charge accumulation portion and the floating diffusion, wherein the charge transmission means is a charge coupled device, and the electric charge in a plurality of sensing charge accumulation portions is transmitted to one floating diffusion.

5. The apparatus for measurement of a physical or chemical phenomenon according to claim 4, further comprising the detection portion having n-diffusion layer formed, or, when the semiconductor portion is p-type substrate, having an electrode constituted on the upper site of the p-type substrate to form a sensing charge accumulation portion.

6. The apparatus for measurement of a physical or chemical phenomenon according to claim 3, further comprising a charge transmission means between the sensing charge accumulation portion and the floating diffusion, wherein the charge transmission means is a charge coupled device, and the electric charge in a plurality of sensing charge accumulation portions is transmitted to one floating diffusion.

7. The apparatus for measurement of a physical or chemical phenomenon according to claim 6, further comprising the detection portion having n-diffusion layer formed, or, when the semiconductor portion is p-type substrate, having an electrode constituted on the upper site of the p-type substrate to form a sensing charge accumulation portion.

8. The apparatus for measurement of a physical or chemical phenomenon according to claim 3, further comprising the detection portion having n-diffusion layer formed, or, when the semiconductor portion is p-type substrate, having an electrode constituted on the upper site of the p-type substrate to form a sensing charge accumulation portion.

9. The apparatus for measurement of a physical or chemical phenomenon according to claim 3, further comprising the detection portion having n-diffusion layer formed, or, when the semiconductor portion is p-type substrate, having an electrode constituted on the upper site of the p-type substrate to form a sensing charge accumulation portion.

10. An apparatus for measuring a physical or chemical phenomenon, comprising:
a charge feeding portion for feeding electric charge to a sensing portion, the sensing portion having voltage changed depending on the magnitude of physical or chemical amount and working as a threshold, and a detection portion having a floating diffusion region for removing the fed electric charge,
a sensing charge accumulation portion interposed between the sensing portion and the floating diffusion region, for accumulating electric charge that is limited by the sensing portion threshold and transmitted from the charge feeding portion via the sensing portion, and having a reset gate for releasing a part of the electric charge that is corresponding to an offset potential or external disturbing component,
a threshold portion for transmitting the remaining electric charge to the floating diffusion,
a detection system A having a sensing portion having potential changed depending on the magnitude of physical or chemical amount, wherein a part of the electric charge fed to the sensing portion is transmitted via the sensing charge accumulation portion and a barrier portion to the floating diffusion region,
a detection system B having a sensing portion not responding to a change in physical or chemical amount and having the same function as in the detection system A except for the sensing portion, and
wherein the amount of electric charge transmitted from the barrier portion in the detection system A is changed by synchronizing with the amount of electric charge accumulated in the sensing charge accumulation portion in the detection system B.

11. The apparatus for measurement of a physical or chemical phenomenon according to claim 10, further comprising a charge transmission means between the sensing charge accumulation portion and the floating diffusion, wherein the charge transmission means is a charge coupled device, and the electric charge in a plurality of sensing charge accumulation portions is transmitted to one floating diffusion.

12. The apparatus for measurement of a physical or chemical phenomenon according to claim 11, further comprising the detection portion having n-diffusion layer formed, or, when the semiconductor portion is p-type substrate, having an electrode constituted on the upper site of the p-type substrate to form a sensing charge accumulation portion.

13. The apparatus for measurement of a physical or chemical phenomenon according to claim 10, further comprising a charge transmission means between the sensing charge accumulation portion and the floating diffusion, wherein the charge transmission means is a charge coupled device, and the electric charge in a plurality of sensing charge accumulation portions is transmitted to one floating diffusion.

14. The apparatus for measurement of a physical or chemical phenomenon according to claim 13, further comprising the detection portion having n-diffusion layer formed, or, when the semiconductor portion is p-type substrate, having an electrode constituted on the upper site of the p-type substrate to form a sensing charge accumulation portion.

15. The apparatus for measurement of a physical or chemical phenomenon according to claim 10, further comprising the detection portion having n-diffusion layer formed, or, when the semiconductor portion is p-type substrate, having an electrode constituted on the upper site of the p-type substrate to form a sensing charge accumulation portion.

16. The apparatus for measurement of a physical or chemical phenomenon according to elaini& claim 10, further comprising the detection portion having n-diffusion layer formed, or, when the semiconductor portion is p-type substrate, having an electrode constituted on the upper site of the p-type substrate to form a sensing charge accumulation portion.

* * * * *